US 6,727,265 B2

(12) United States Patent
Uckun et al.

(10) Patent No.: US 6,727,265 B2
(45) Date of Patent: Apr. 27, 2004

(54) PHENOXYETHYL-THIOUREA-PYRIDINE COMPOUNDS AND THEIR USE FOR TREATMENT OF HIV-INFECTIONS

(75) Inventors: Fatih M. Uckun, White Bear Lake, MN (US); Taracad K. Venkatachalam, Maplewood, MN (US)

(73) Assignee: Parker Hughes Institute, Roseville, MN (US)

( * ) Notice: Subject to any disclaimer, the term of this patent is extended or adjusted under 35 U.S.C. 154(b) by 0 days.

(21) Appl. No.: 10/420,032

(22) Filed: Apr. 15, 2003

(65) Prior Publication Data

US 2003/0186991 A1 Oct. 2, 2003

Related U.S. Application Data

(63) Continuation of application No. PCT/US00/41209, filed on Oct. 18, 2000.
(51) Int. Cl.[7] .................. A61K 31/44; C07D 213/72
(52) U.S. Cl. .................. 514/353; 546/305; 546/306; 546/297; 546/292; 435/184; 514/349
(58) Field of Search ................. 514/353, 349; 546/305, 306, 297, 292; 435/184

(56) References Cited

U.S. PATENT DOCUMENTS 6,207,688 B1 * 3/2001 Uckum et al. .............. 514/352

OTHER PUBLICATIONS

Venkatachalam, T.K. et al. : Piperidinylethyl, Phenoxyethyl and fluoroethyl bromopyridyl thiourea compounds with potent anti–HIV activity. Antiviral Chem. & Chemother. vol. 11, pp. 329–336, 2000.*

* cited by examiner

Primary Examiner—Charaiyit S. Aulakh
(74) Attorney, Agent, or Firm—Merchant & Gould P.C.

(57) ABSTRACT

The invention provides compounds which inhibit reverse transcriptase (RT) and which inhibit replication of a retrovirus, such as human immunodeficiency virus-1 (HIV-1). The compound of the invention are phenoxyethyl-thiourea-pyridines. The invention additionally provides a method for inhibiting reverse transcriptase activity of a retrovirus, such as HIV-1, comprising contacting the retrovirus with a compound of the invention. The invention additionally provides a method for inhibiting replication of a retrovirus, such as HIV-1, comprising contacting the retrovirus with a compound of the invention.

21 Claims, No Drawings

PHENOXYETHYL-THIOUREA-PYRIDINE COMPOUNDS AND THEIR USE FOR TREATMENT OF HIV-INFECTIONS

This application is a continuation of PCT/US00/41206, filed Oct. 18, 2000.

FIELD OF THE INVENTION

The invention relates to compounds as non-nucleoside inhibitors of reverse transcriptase that are effective against HIV, including mutant strains of HIV, and effective in the treatment of multi-drug resistant HIV infection.

BACKGROUND OF THE INVENTION

Agents currently used to treat HIV infection attempt to block replication of the HIV virus by blocking HIV reverse transcriptase or by blocking HIV protease. Three categories of anti-retroviral agents in clinical use are nucleoside analogs (such as AZT), protease inhibitors (such as nelfinavir), and the recently introduced non-nucleoside reverse transcriptase inhibitors (NNI), such as nevirapine.

The recent development of potent combination antiretroviral regimens has significantly improved prognosis for persons with HIV and AIDS. Combination therapies may be a significant factor in the dramatic decrease in deaths from AIDS (a decrease in death rate as well as absolute number). The most commonly used combinations include two nucleoside analogs with or without a protease inhibitor.

Nevirapine is currently the only NNI compound which has been used in combination with AZT and/or protease inhibitors for the treatment of HIV. A new series of effective drug cocktails will most likely involve other NNIs in combination with nucleoside and protease inhibitors as a triple action treatment to combat the growing problem of drug resistance encountered in single drug treatment strategies.

The high replication rate of the virus unfortunately leads to genetic variants (mutants), especially when selective pressure is introduced in the form of drug treatment. These mutants are resistant to the anti-viral agents previously administered to the patient. Switching agents or using combination therapies may decrease or delay resistance, but because viral replication is not completely suppressed in single drug treatment or even with a two drug combination, drug-resistant viral strains ultimately emerge. Triple drug combinations employing one (or two) nucleoside analogs and two (or one) NNI targeting RT provide a very promising therapy to overcome the drug resistance problem. RT mutant strains resistant to such a triple action drug combination would most likely not be able to function.

Dozens of mutant strains have been characterized as resistant to NNI compounds, including L1001, K103N, V106A, E138K, Y181C and Y188H. In particular, the Y181C and K103N mutants may be the most difficult to treat, because they are resistant to most of the NNI compounds that have been examined.

Recently, a proposed strategy using a knock-out concentration of NNI demonstrated very promising results. The key idea in this strategy is to administer a high concentration of NNI in the very beginning stages of treatment to reduce the virus to undetectable levels in order to prevent the emergence of drug-resistant strains. The ideal NNI compound for optimal use in this strategy and in a triple action combination must meet three criteria:

1) very low cytotoxicity so it can be applied in high doses;
2) very high potency so it can completely shut down viral replication machinery before the virus has time to develop resistant mutant strains; and
3) robust anti-viral activity against current clinically observed drug resistant mutant strains.

Novel NNI designs able to reduce RT inhibition to subnanomolar concentrations with improved robustness against the most commonly observed mutants and preferably able to inhibit the most troublesome mutants are urgently needed. New antiviral drugs will ideally have the following desired characteristics: (1) potent inhibition of RT; (2) minimum cytotoxicity; and (3) improved ability to inhibit known, drug-resistant strains of HIV. Currently, few anti-HIV agents possess all of these desired properties.

Two non-nucleoside inhibitors (NNI) of HIV RT that have been approved by the U.S. Food and Drug Administration for licensing and sale in the United States are nevirapine (dipyridodiazepinone derivative) and delavirdine (bis(heteroaryl)piperazine (BHAP) derivative, BHAP U-90152). Other promising new non-nucleoside inhibitors (NNIs) that have been developed to inhibit HIV RT include dihydroalkoxybenzyloxopyrimidine (DABO) derivatives, 1-[(2-hydroxyethoxy)methyl]-6-(phenylthio)thymine (HEPT) derivatives, tetrahydrobenzondiazepine (TIBO), 2',5'-Bis-O-(tert-butyidimethylsilyl)-3'-spiro-5"-(4"-amino-1",2"-oxathiole-2",2'-dioxide)pyrimidine (TSAO), oxathiin carboxanilide derivatives, quinoxaline derivatives, thiadiazole derivatives, and phenethyltilazolylthiourea (PETT) derivatives.

NNIs have been found to bind to a specific allosteric site of HIV-RT near the polymerase site and interfere with reverse transcription by altering either tile conformation or mobility of RT, thereby leading to a noncompetitive inhibition of the enzyme (Kohlstaedt, L. A. et al., *Science*, 1992, 256, 1783–1790).

A number of crystal structures of RT complexed with NNIs have been reported (including α-APA, TIBO, Nevirapine, and HEPT derivatives), and such structural information provides the basis for further derivatization of NNI aimed at maximizing binding affinity to RT. However, the number of available crystal structures of RT NNI complexes is limited.

SUMMARY OF THE INVENTION

The invention provides substituted and unsubstituted phenoxyethyl-thiourea-pyridine compounds which inhibit reverse transcriptase (RT) and which inhibit replication of a retrovirus, such as human immunodeficiency virus-1 (HIV-1).

The invention additionally provides a method for inhibiting reverse transcriptase activity of a retrovirus, such as HIV-1, comprising contacting the retrovirus with a compound of the invention. The invention additionally provides a method for inhibiting replication of a retrovirus, such as HIV-1, comprising contacting the retrovirus with a compound of the invention. The invention also provides a method for treating a retroviral infection in a subject, such as an HIV-1 infection, comprising administering a compound of the invention to the subject.

The invention also provides compositions comprising a compound or inhibitor of the invention, and optionally, an acceptable carrier. In one embodiment, the composition is a pharmaceutical composition.

DETAILED DESCRIPTION OF THE INVENTION

Definitions

All scientific and technical terms used in this application have meanings commonly used in the art unless otherwise specified. As used in this application, the following words or phrases have the meanings specified.

As used herein, a "retrovirus" includes any virus that expresses reverse transcriptase. Examples of a retrovirus include, but are not limited to, HIV-1, HIV-2, HTLV-I, HTLV-II, FeLV, FIV, SIV, AMV, MMTV, and MoMuLV.

As used herein, "reverse transcriptase (RT)" refers to an enzyme having a non-nucleoside inhibitor (NNI) binding site similar to that of HIV-1 RT and to which ligands which bind the composite binding pocket of the invention bind.

As used herein, "reverse transcriptase (RT) activity" means the ability to effect reverse transcription of retroviral RNA to proviral DNA. One means by which RT activity can be determined is by measuring viral replication. One measure of viral replication is the p24 assay described herein.

As used herein, a compound that "inhibits replication of human immunodeficiency virus (HIV)" means a compound that, when contacted with HIV-1, for example, via HIV-infected cells, effects a reduction in the amount of HIV-1 as compared with untreated control. Inhibition of replication of HIV-1 can be measured by various means known in the art, for example, the p24 assay disclosed herein.

As used herein, a "nonnucleoside inhibitor (NNI)" of HIV reverse transcriptase (HIV-RT) means a compound which binds to an allosteric site of HIV-RT, leading to noncompetitive inhibition of HIV-RT activity. Examples of non-nucleoside inhibitors of HIV-RT include, but are not limited to, tetrahydroimidazobenzodiazepinthiones (TIBO), 1-[(2-hydroxyethoxy)methyl]-6-(phenylthio)thynines (HEPT), bis (heteroaryl)piperazines (BHAP), 2'-5'-bis-O-(tertbutyldimethylsilyl)-3'-spiro-5"-(4"-amino-1", 2"-oxathiole-2", 2"-dioxide)pyrimidines (TSAO), dihydroalkoxybenzyloxopyrimidine (DABO) and phenethylthiazolylthiourea (PETT) analogs. The nonnucleoside inhibitor of HIV-RT of this invention are substituted and unsubstituted phenoxyethyl-thiourea-pyridine compounds As used herein, "derivative" means a chemical substance derivable from a parent substance by addition or substitution of components and which maintains the activity of the parent substance.

As used herein, "halogen" includes fluoro, chloro, bromo and iodo.

As used herein, "pharmaceutically acceptable salt" refers to a salt that retains the desired biological activity of the parent compound and does not impart any undesired toxicological effects. Examples of such salts include, but are not limited to, (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, furmaric acid, gluconic acid, citric acid, malic acid, ascorbic acid, benzoic acid, tannic acid, pamoic acid, alginic acid, polyglutamic acid, naphthalenesulfonic acids, naphthalene-disulfonic acids, polygalacturonic acid; (b) salts with polyvalent metal cations such as zinc, calcium, bismuth, barium, magnesium, aluminum, copper, cobalt, nickel, cadmium, and the like; or (c) salts formed with an organic cation formed from N,N'-dibenzylethylenediamine or ethylenediamine; or (d) combinations of (a) and (b) or (c), e.g., a zinc tannate salt; and the like. The preferred acid addition salts are the trifluoroacetate salt and the acetate salt.

As used herein, "pharmaceutically acceptable carrier" includes any material which, when combined with a compound of the invention, allows the compound to retain biological activity, such as the ability to inhibit RT activity, and is non-reactive with the subject's immune system. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline. Compositions comprising such carriers are formulated by well known conventional methods (see, for example, Remington's Pharmaceutical Sciences, Chapter 43, 14th Ed., Mack Publishing Col, Easton Pa. 18042, USA).

Compounds of the Invention

Compounds of the invention are phenoxyethyl-thiourea-pyridine compounds that are useful as non-nucleoside inhibitors of reverse transcriptase. The compounds were designed as inhibitors of HIV-1 RT, based on a composite binding pocket computer model constructed from nine (9) individual crystal structures of RT-NNI complexes [51, 52]. Modeling studies for rational drug design included the construction of a composite NNI binding pocket for nine RT-NNI crystal structures, the analyses of surface complementarity between NNIs and RT, and application of inhibitory constants ($K_1$, values) combined with a docking procedure involving the novel thiourea compounds [51, 52]. This computational approach allowed the identification of several ligand derivatization sites for the generation of more potent dual-function thiourea compounds. Detailed analysis of trovirdine-binding [51], revealed multiple, specific sites which where larger functional groups could be incorporated in to the NNI. The composite binding pocket, the docked trovirdine molecule showed abundant sterically allowed usable space surrounding the pyridyl ring, the ethyl linker, and near the 5'-bromo position.

The compounds of the invention are phenoxyethyl-thiourea-pyridine compounds useful as non-nucleoside inhibitors of reverse transcriptase having the formula I:

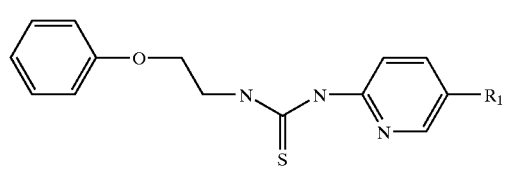

I

The pyridine may be unsubstituted or substituted. For example R' can be hydrogen, hydroxyl or halo.

Preferred compounds of the invention include N-[2-(Phenoxy)ethyl]-N'-[2-(pyridyl)]thiourea (compound II), N-[2-(Phenoxy)ethyl]-N'-[2-(5-chloropyridyl)]thiourea (compound III), N-[2-(Phenoxy)ethyl]-N'-[2-(5-bromopyridyl)]thiourea (compound IV).

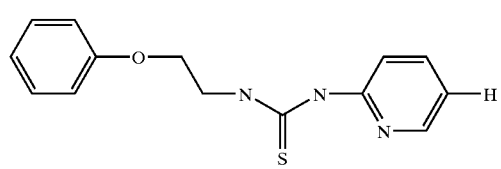

II

-continued

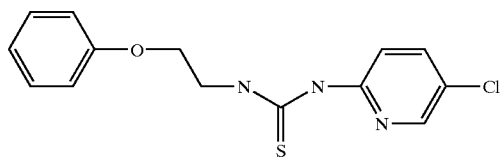

III

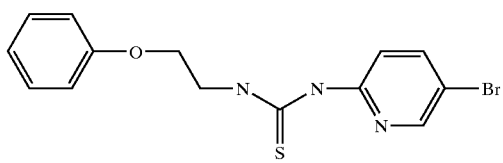

IV

The compounds of the invention have the ability to inhibit replication of a retrovirus, such as human immunodeficiency virus (HIV). In one embodiment, the compound inhibits replication of HIV with an $IC_{50}$ of less than 50 µM, as determined by p24 enzyme immunoassay. In another embodiment, the compound inhibits replication of HIV with an $IC_{50}$ of less than 5 µM. In another embodiment, the compound inhibits replication of HIV with an $IC_{50}$ of less than 1 µM. In yet another embodiment, the compound inhibits replication of HIV with an $IC_{50}$ of less than 5 nM. In another embodiment, the compound inhibits replication of HIV with an $IC_{50}$ of less than 1 nM.

The invention provides a composition comprising a compound or inhibitor of the invention, and optionally, an acceptable carrier. In one embodiment, the composition is a pharmaceutical composition. Compositions of the invention are useful for prevention and treatment of retroviral infection, such as HIV infection.

Methods of Using the Compounds of the Invention

The compounds of the invention are useful in methods for inhibiting reverse transcriptase activity of a retrovirus. Retroviral reverse transcriptase is inhibited by contacting RT in vitro or in vivo, with an effective inhibitory amount of a compound of the invention. The compounds of the invention also inhibit replication of retrovirus, particularly of HIV, such as HIV-1. Viral replication is inhibited, for example, by contacting the virus with an effective inhibitory amount of a compound of the invention.

The methods of tile invention are useful for inhibiting reverse transcriptase and/or replication of multiple strains of HIV, including mutant strains, and include treating a retroviral infection in a subject, such as an HIV-1 infection, by administering an effective inhibitory amount of a compound or a pharmaceutically acceptable acid addition salt of a compound of the Formula I. The compound or inhibitor of Formula I is preferably administered in combination with a pharmaceutically acceptable carrier, and may be combined with specific delivery agents, including targeting antibodies and/or cytokines. The compound or inhibitor of the invention may be administered in combination with other antiviral agents, immunomodulators, antibiotics or vaccines.

The compounds of Formula I can be administered orally, parentally (including subcutaneous injection, intravenous, intramuscular, intrasternal or infusion techniques), by inhalation spray, topically, by absorption through a mucous membrane, or rectally, in dosage unit formulations containing conventional non-toxic pharmaceutically acceptable carriers, adjuvants or vehicles. Pharmaceutical compositions of the invention can be in the form of suspensions or tablets suitable for oral administration, nasal sprays, creams, sterile injectable preparations, such as sterile injectable aqueous or oleagenous suspensions or suppositories. In one embodiment, the TET compounds of the invention can be applied intravaginally and/or topically, for example in gel form, for prevention of heterosexual transmission of HIV.

For oral administration as a suspension, the compositions can be prepared according to techniques well-known in the art of pharmaceutical formulation. The compositions can contain microcrystalline cellulose for imparting bulk, alginic acid or sodium alginate as a suspending agent, methylcellulose as a viscosity enhancer, and sweeteners or flavoring agents. As immediate release tablets, the conpositions can contain microcrystalline cellulose, starch, magnesium stearate and lactose or other excipients, binders, extenders, disintegrants, diluents and lubricants known in the art.

For administration by inhalation or aerosol, the compositions can be prepared according to techniques well-known in the art of pharmaceutical formulation. The compositions can be prepared as solutions in saline, using benzyl alcohol or other suitable preservatives, absorption promoters to enhance bioavailability, fluorocarbons or other solubilizing or dispersing agents known in the art.

For administration as injectable solutions or suspensions, the compositions can be formulated according to techniques well-known in the art, using suitable dispersing or wetting and suspending agents, such as sterile oils, including synthetic mono- or diglycerides, and fatty acids, including oleic acid.

For rectal administration as suppositories, the compositions can be prepared by mixing with a suitable non-irritating excipient, such as cocoa butter, synthetic glyceride esters or polyethylene glycols, which are solid at ambient temperatures, but liquefy or dissolve in the rectal cavity to release the drug.

Dosage levels of approximately 0.02 to approximately 10.0 grams of a compound of the invention per day are useful in the treatment or prevention of retroviral infection, such as HIV infection, AIDS or AIDS-related complex (ARC), with oral doses 2 to 5 times higher. For example, HIV infection can be treated by administration of from about 0.1 to about 100 milligrams of compound per kilogram of body weight from one to four times per day. In one embodiment, dosages of about 100 to about 400 milligrams of compound are administered orally every six hours to a subject. The specific dosage level and frequency for any particular subject will be varied and will depend upon a variety of factors, including the activity of the specific compound the metabolic stability and length of action of that compound, the age, body weight, general health, sex, and diet of the subject, mode of administration, rate of excretion, drug combination, and severity of the particular condition.

The compounds of Formula I can be administered in combination with other agents useful in the treatment of HIV infection, AIDS or ARC. For example, the compound of the invention can be administered in combination with effective amounts of an antiviral, immunomodulator, anti-infective, or vaccine. The compound of the invention can be administered prior to, during, or after a period of actual or potential exposure to retrovirus, such as HIV.

Conjugation to a Targeting Moiety

The compound of the invention can be targeted for specific delivery to the cells to be treated by conjugation of the compounds to a targeting moiety. Targeting moiety useful for conjugation to the compounds of the invention include antibodies, cytokines, and receptor ligands expressed on the cells to be treated.

The term "conjugate" means a complex formed with two or more compounds.

The phrase "targeting moiety" means a compound which serves to deliver the compound of the invention to a specific site for the desired activity. Targeting moieties include, for example, molecules which specifically bind molecules present on a cell surface. Such targeting moieties useful in the invention include anti-cell surface antigen antibodies. Cytokines, including interleukins, factors such as epidermal growth factor (EGF), and the like, are also specific targeting moieties known to bind cells expressing high levels of their receptors.

Particularly useful targeting moieties for targeting the compounds of the invention to cells for therapeutic activity include those ligands that bind antigens or receptors present on virus-infected cells to be treated. For example, antigens present on T-cells, such as CD48, can be targeted with antibodies. Antibody fragments, including single chain fragments, can also be used. Other such ligand-receptor binding pairs are known in the scientific literature for targeting anti-viral treatments to target cells. Methods for producing conjugates of the compounds of the invention and the targeting moieties are known.

Methods of Making the Compounds of the Invention

The compounds of the invention are prepared as follows. First an amine substituted pyridine is reacted with thiocarbonyldiimidazole in acetonitrile at room temperature. The reaction precipitate is then filtered to yield the thiocarbonyl intermediate. Dimethyl formamide was then added to the thiocarbonyl intermediate to create a solution. An appropriate amime was then added to the thiocarbonyl intermediate solution, and the resulting solution was heated. The solution was cooled, precipitated, filtered, and the solvent evaporated to yield the desired thiourea compound. The compounds were further purified by column chromatography. The compounds of the invention are prepared as depicted in Scheme 1 below:

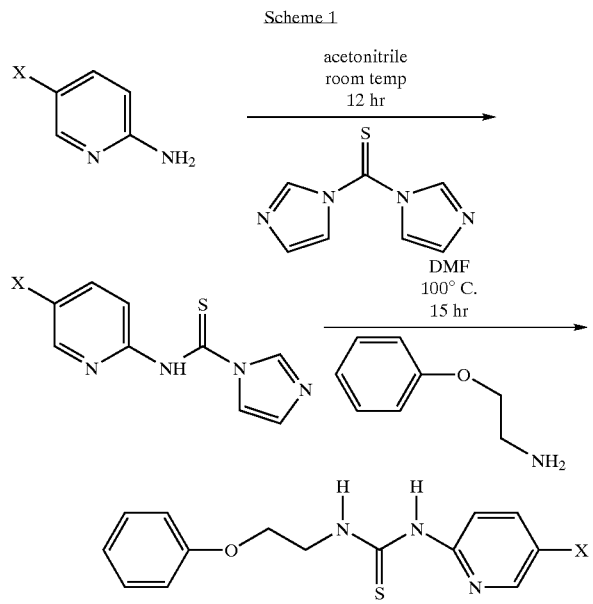

Scheme 1

EXAMPLES

The following examples are presented to illustrate the present invention and to assist one of ordinary skill in making and using the same. The examples are not intended in any way to otherwise limit the scope of the invention.

Example 1

Synthesis and Characterization of Compounds of the Invention

All chemicals were purchased from the Aldrich Chemical Company, Milwaukee, Wis., and were used directly for synthesis. Anhydrous solvents such as acetonitrile, methanol, ethanol, ethyl acetate, tetrahydrofuran, chloroform, and methylene chloride were obtained from Aldrich as sure seal bottles under nitrogen and were transferred to reaction vessels by cannulation. All reactions were carried out under nitrogen atmosphere.

Synthesis of Compounds

The general synthesis from Scheme I above was followed. The specific amine substituted pyridines utilized to make Compounds I, II, and III respectively were 2-aminopyridine, 2-amino-5-chloropyridine, and 2-amino-5-bromopyridine.

Specifically, thiocarbonyldiimidazole (8.90 g, 50 mmol) and the amino substituted pyridine (50 mmol) were added to 50 mL of dry acetonitrile at room temperature. The reaction mixture was stirred for 12 hours and the precipitate filtered, washed with cold acetonitrile (2×25 mL), and dried under vacuum to afford (1 1.40 g, 80% ) of compound A. To a suspension of compound A (0.55 eqv) in dimethyl formamide (15 mL) an appropriate amine (0.50 eqv) was added. The reaction mixture was heated to 100° C. and stiffed for 15 hours. The reaction mixture was poured into ice-cold water and the suspension was stirred for 30 minutes. The product was filtered, washed with water, dried, and further purified by column chromatography to furnish the target compounds in good yields. Trovidine, a comparative standard, was prepared by the method described in Bell et al., *J Med. Chem* 1995,38:4926–9; Ahgren et.al., 1995, *Antimiclob.Agents Chemotherapy* 39:1329–1335.

Characterization of Compounds

Proton and carbon nuclear magnetic resonance spectra were recorded on a Varian spectrometer using an automatic broad band probe. Unless otherwise noted, all NMR spectra were recorded in $CDCl_3$ at room temperature. The chemical shifts reported are in parts per million relative to tetramethyl silane as standard. The multiplicity of the signals were designated as follows: s, d, dd, t, q, m which corresponds to singlet, doublet, doublet of doublet, triplet, quartet and multiplet respectively. UV spectra were recorded from a Beckmann Model # DU 7400 UV/Vis spectrometer using a cell path length of 1 cm. Fourier Transform Infrared spectra were recorded using an FT-Nicolet model Protege #460 instrument. The infrared spectra of the liquid samples were run as neat liquids using KBr discs. Mass spectrum analysis was conducted using either a Finnigan MAT 95 instrument or a Hewlett-Packard Matrix Assisted Laser Desorption (MALDI) spectrometer model # G2025A The matrix used in the latter case was cyano hydoxy cinnamic acid. Melting points were determined using a Melt John's apparatus and uncorrected. Elemental analysis was performed by Atlantic Microlabs (Norcross, Ga.). Column chromatography was performed using silica gel obtained from the Baker Company. The solvents used for elution varied depending on the compound and included one of the following: ethyl acetate, methanol, chloroform, hexane, methylene chloride and ether. Characterization data for the synthesized compounds is shown below:

N-[12-(Phenoxy)ethyl]-N'-[2-(pyridyl)thiourea (compound II)

Yield 60%; mp. 168.5–170.5° C.; UV(MeOH)$\gamma_{max}$224, 246, 267, 293 nm; IR v 3232, 3045, 2931, 1602, 1560, 1481, 1317, 1245, 1080, 773, 668 cm$^{-1}$;$^1$H NMR (DMSO) δ 11.98 (t, 1H), 10.67 (s, 1H), 8.17 (dd. 1H, J=5.4), 7.88–7.73 (m, 1H), 7.31–7.17 (m, 2H), 7.15 (dd. 1H, J=8.4), 7.04–6.90 (m, 4H), 4.19 (t, 2H) 4.00 (q, 2H); $^{13}$C NMR (DMSO-$d_6$) δ 179.8. 158.2, 153.7, 145.5, 139.0, 129.6, 120.9, 118.0, 114.6, 112.6, 65.7, 44.0; MALDI-TOF: 275.0.

N-[2-(Phenoxy)ethyl]-N'-[2-(5-chloropyridyl) thiourea. (compound III)

Yield 65%; mp. 168–169° C.; UV (MeOH)$\gamma_{max}$: 245, 265 nm; IR v 3221, 3161, 3088, 3037, 2933, 2875, 1601, 1562, 1533, 1477, 1407, 1359, 1305, 1263, 1238, 1194, 1136, 1111, 1047, 908, 862, 821, 750, 690 cm$^{-1}$;$^1$H NMR (DMSO-$d_6$) δ 11.50 (t, 1H), 10.83 (s, 1H), 8.19 (d, 1H, J=2.7), 7.86 (dd, 1H, J=8.7), 7.28 (q, 2H), 7.20 (d, 1H, J=9), 7.00–6.90 (m, 3H), 4.19 (t, 2H), 3.99 (q, 2H);$^{13}$C NMR (DMSO-$d_6$) δ 179.6, 158.2, 152.1, 143.8, 138.9, 129.6, 123.9, 120.9, 114.6, 114.2, 65.6, 44.1.

N-[2-(Phenoxy)ethyl]-N'-[2-(5-bromopyridyl)] thiourea (compound IV)

Yield 56%; mp.162–163° C.; UV (MeOH)$\gamma_{max}$: 249, 268 nm; IR v 3219, 3161 3084, 3032, 2929, 2875, 1599, 1560, 1527, 1468 1356, 1307, 1278, 1238, 1191, 1138, 1078, 1047, 1005, 951, 860, 821, 752, 690 cm$^{-1}$; $^1$H NMR (DMSO-$d_6$) δ 11.48 (t, 1H), 10.82 (s, 1H), 8.26 (d, 1H, J=2.4), 7.97 (dd, 1H, J=9), 7.27 (q, 2H), 7.14 (dd, 1H, J=8.7), 7.00–6.90 (m, 3H), 4.18 (t, 2H), 3.99 (q, 2H;$^{13}$C NMR (DMSO-$d_6$) δ 179.6, 158.2, 152.3, 146.0, 141.5, 129.6, 120.9, 114.6, 112.1, 65.6, 44.2.

Example 2

In vitro Inhibition of Reverse Transcriptase by the Compounds of the Invention

The synthesized compounds were tested for RT inhibitory activity ($IC_{50}$[rRT]) against purified recombinant HIV RT using the cell-free Quan-T-RT system (Amersham, Arlington Heights, Ill.), which utilizes the scintillation proximity assay principle as described in Bosworth, et al., 1989, *Nature* 341:167–168. In the assay, a DNA/RNA template is bound to SPA beads via a biotin/strepavidin linkage. The primer DNA is a 16-mer oligo(T) which has been annealed to a poly(A) template. The primer/template is bound to a strepavidin-coated SPA bead.

$^3$H-TTP is incorporated into the primer by reverse transcription. In brief, $^3$H-TTP, at a final concentration of 0.5 μCi/sample, was diluted in RT assay buffer (49.5 mM Tris-Cl, pH 8.0, 80 mM KCl, 10 Mm $MgCl_2$, 10 mM DTT, 2.5 mM EGTA, 0.05% Nonidet-P-40), and added to annealed DNA/RNA bound to SPA beads. The compound being tested was added to the reaction mixture at 0.001 μM-100 μM concentrations. Addition of 10 mU of recombinant HIV RT and incubation at 37° C. for 1 hour resulted in tile extension of the primer by incorporation of $^3$H-TTP. The reaction was stopped by addition of 0.2 ml of 120 mM EDTA. The samples were counted in an open window using a Beckman LS 7600 instrument and $IC_{50}$ values were calculated by comparing the measurements to untreated samples.

In addition, the anti-HIV activity of the compounds was measured by determining their ability to inhibit the replication of the HIV-1 strain HTLVIIIB in peripheral blood mononuclear cells (PBMC) from healthy volunteer donors, using the method described in Uckun et.al., 1998, *Antimicrobial Agents and Chemotherapy* 42:383. The HIV strain HTLVIIIB was kindly provided by Dr. Neal T.Wetherall, VIROMED Laboratories, Inc., and was propagated in CCRF-CEM cells.

The data are shown in Table 1A. Compounds II, III, and IV each exhibited promising anti-HIV activity with 100% inhibition at concentrations ≧1 μM, minimal cytotoxicity with $CC_{50}$ values ranging from 30 to >100 μM, and selectivity indices ranging from 1100 to >50,000. Compared with phenethyl thiourea pyridine compounds (shown in Table 1B below) the phenoxyethyl thiourea pyridine compounds have greater potency. Taken together, these results provide evidence that the structural features of the "bridge" between the pyridyl and phenyl moieties of PETT-related thiourea compounds significantly affects their biologic activity as NNI of HIV-1 RT.

TABLE 1A

HIV-RT inhibitory activity of the compounds of the invention

| Compound Number | Structure | IC$_{50}$[rRT] μM | IC$_{50}$ [HTLV$_{HIB}$] μm | CC μM | SI |
|---|---|---|---|---|---|
| II | phenyl-O-CH$_2$CH$_2$-NH-C(=S)-NH-(5-H-pyridin-2-yl) | 10.1 | 0.005 | 55 | 1,100 |
| III | phenyl-O-CH$_2$CH$_2$-NH-C(=S)-NH-(5-Cl-pyridin-2-yl) | 1.5 | 0.004 | >100 | >25,000 |
| IV | phenyl-O-CH$_2$CH$_2$-NH-C(=S)-NH-(5-Br-pyridin-2-yl) | 1.5 | 0.005 | 92 | 18,400 |
| Troviridine | phenyl-CH$_2$CH$_2$-NH-C(=S)-NH-(5-Br-pyridin-2-yl) | ND | 0.007 | 100 | 14,286 |

TABLE 1B

HIV-RT inhibitory activity of phenethyl thiourea pyridine compounds.

| Compound Number | Structure | IC$_{50}$[rRT] μM | IC$_{50}$ [HTLV$_{HIB}$] μm | CC μM | SI |
|---|---|---|---|---|---|
| V | 4-Cl-phenyl-CH$_2$CH$_2$-NH-C(=S)-NH-(5-Br-pyridin-2-yl) | 2.5 | 20.8 | N.D. | N.D. |
| VII | 4-OH-phenyl-CH$_2$CH$_2$-NH-C(=S)-NH-(5-Br-pyridin-2-yl) | 87.7 | 3.067 | >100 | N.D. |
| Troviridine | phenyl-CH$_2$CH$_2$-NH-C(=S)-NH-(5-Br-pyridin-2-yl) | 0.8 | 0.007 | >100 | N.D. |

We claim:

1. A compound of the formula:

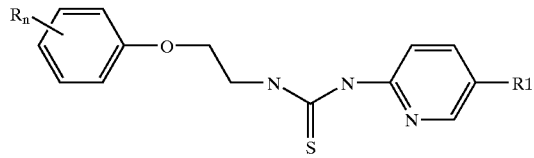

wherein
R¹ is H, hydroxyl or halo;
n is an integer from 0 to 5;
R is $C_1$–$C_6$ alkyl, alkoxy, hydroxyl, amino, or halo.

2. A compound of claim 1 wherein
$R_1$ is hydrogen or a halo;
and n is 0.

3. A compound of the formula:

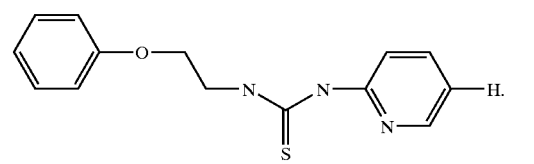

4. A compound of the formula:

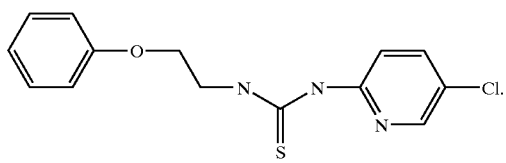

5. A compound of the formula:

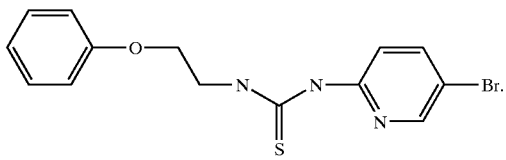

6. A pharmaceutical composition comprising a therapeutically effective amount of the compound of claim 1 and a pharmaceutically acceptable carrier or diluent.

7. A pharmaceutical composition comprising a therapeutically effective amount of the compound of claim 3 and a pharmaceutically acceptable carrier or diluent.

8. A pharmaceutical composition comprising a therapeutically effective amount of the compound of claim 4 and a pharmaceutically acceptable carrier or diluent.

9. A pharmaceutical composition comprising a therapeutically effective amount of the compound of claim 5 and a pharmaceutically acceptable carrier or diluent.

10. A method for inhibiting HIV reverse transcriptase comprising contacting said HIV with an effective HIV reverse transcriptase inhibitory amount of a compound of claim 1.

11. A method for inhibiting HIV reverse transcriptase comprising contacting said HIV with an effective HIV reverse transcriptase inhibitory amount of a compound of claim 3.

12. A method for inhibiting HIV reverse transcriptase comprising contacting said HIV with an effective HIV reverse transcriptase inhibitory amount of a compound of claim 4.

13. A method for inhibiting HIV reverse transcriptase comprising contacting said HIV with an effective HIV reverse transcriptase inhibitory amount of a compound of claim 5.

14. A method for treating HIV infection in a subject comprising administering to said subject an anti-HIV effective amount of a compound of claim 1.

15. A method for treating HIV infection in a subject comprising administering to said subject an anti-HIV effective amount of a compound of claim 3.

16. A method for treating HIV infection in a subject comprising administering to said subject an anti-HIV effective amount of a compound of claim 4.

17. A method for treating HIV infection in a subject comprising administering to said subject an anti-HIV effective amount of a compound of claim 5.

18. A method for treating drug-resistant HIV in a subject comprising administering to said subject a drug-resistant HIV treating effective amount of claim 1.

19. A method for treating drug-resistant HIV in a subject comprising administering to said subject a drug-resistant HIV treating effective amount of claim 3.

20. A method for treating drug-resistant HIV in a subject comprising administering to said subject a drug-resistant HIV treating effective amount of claim 4.

21. A method for treating drug-resistant HIV in a subject comprising administering to said subject a drug-resistant HIV treating effective amount of claim 5.

* * * * *

UNITED STATES PATENT AND TRADEMARK OFFICE
CERTIFICATE OF CORRECTION

PATENT NO. : 6,727,265 B2  
DATED : April 27, 2004  
INVENTOR(S) : Uckun et al.

Page 1 of 1

It is certified that error appears in the above-identified patent and that said Letters Patent is hereby corrected as shown below:

Title page,
Item [56], References Cited, U.S. PATENT DOCUMENTS, insert:
-- 5,593,993   01/1997   Morin, Jr. et al.
6,124,324   09/2000   Uckun et al. -- in appropriate order
OTHER PUBLICATIONS, insert:

--Ahgren, C. et al., "The PETT Series, a New Class of Potent Nonnucleoside Inhibitors of Human Immunodeficiency Virus Type 1 Reverse Transcriptase," *Antimicrobial Agents and Chemotherapy*, Vol 39, No. 6, pp. 1329-1335 (June 1995).

Bell, F.W. et al., "Phenethylthiazolethiourea (PETT) Compounds, a New Class of HIV-1 Reverse Transcriptase Inhibitors. 1. Synthesis and Basic Structure -- Activity Relationship Studies of PETT Analogs," *J. Med. Chem.*, Vol. 38, No. 25, pp. 4929-4936 (1995).

Bosworth, N. et al., "Scintillation proximity assay," *Nature*, Vol. 341, pp. 167-168 (September 14, 1989).

Cantrell, A.S. et al., "Phenethylthiazolylthiourea (PETT) Compounds as a New Class of HIV-1 Reverse Transcriptase Inhibitors. 2. Synthesis and Further Structure -- Activity Relationship Studies of PETT Analogs," *J. Med. Chem.*, Vol. 39, No. 21, pp. 4261-4274 (1996).

Notification of Transmittal of the International Search Report or the Declaration for International Application No. PCT/US00/41209, 10 pages, mailed May 31, 2001.

Kohlstaedt, L.A. et al., "Crystal Structure at 3.5 Å Resolution of HIV-1 Reverse Transcriptase Complexed with an Inhibitor," *Science*, Vol. 256, pp. 1783-1790 (June 26, 1992).

Uckun, F.M. et al., "TXU (Anti-CD7)-Pokeweed Antiviral Protein as a Potent Inhibitor of Human Immunodeficiency Virus," *Antimicrobial Agents and Chemotherapy*, Vol. 42, No. 2, pp. 383-388 (February 1998).-- in appropriate order Column 5,
Line 47, "methods of tile invention" should read -- methods of the invention --

Column 9,
Line 15, "muItiplet respectively." should read -- multiplet respectively. --

Signed and Sealed this

Tenth Day of August, 2004

JON W. DUDAS
*Acting Director of the United States Patent and Trademark Office*